United States Patent [19]
Sackner

[11] 3,945,385
[45] Mar. 23, 1976

[54] SUCTION CATHETER

[75] Inventor: Marvin A. Sackner, Miami Beach, Fla.

[73] Assignee: Physicians' Medical Patent Development Corporation, Newark, N.J.

[22] Filed: Oct. 25, 1974

[21] Appl. No.: 518,154

[52] U.S. Cl. ............................. 128/350 R; 128/276
[51] Int. Cl.² ........................................ A61M 25/00
[58] Field of Search ............ 128/350 R, 349 R, 348, 128/351, 240, 239, 276

[56] References Cited
UNITED STATES PATENTS

| 1,626,839 | 5/1927 | Kallmeyer | 128/239 |
| 1,638,532 | 8/1927 | Kallmeyer | 128/239 |
| 2,568,566 | 9/1951 | Sokolik | 128/240 |
| 2,711,740 | 6/1955 | Pickens | 128/349 R |
| 3,136,316 | 6/1964 | Beall | 128/350 R |
| 3,319,628 | 5/1967 | Halligan | 128/276 |
| 3,848,604 | 11/1974 | Sackner | 128/350 R |

Primary Examiner—Dalton L. Truluck
Attorney, Agent, or Firm—Holman & Stern

[57] ABSTRACT

A suction catheter in which an elongate flexible plastic tube having an open distal tip is provided with axially extending flanges at its distal end with apertures extending through the wall of the catheter between the flanges.

10 Claims, 8 Drawing Figures

SUCTION CATHETER

BACKGROUND OF THE INVENTION

This invention relates to medical catheters, and more particularly to suction catheters for safe tracheobronchial and nasopharyngeal suctioning.

Damage caused to the tracheobronchial mucosa by routine suctioning with conventional suction catheters is well documented. U.S. Pat. No. 3,848,604 granted Nov. 19, 1974 to Marvin A. Sackner, discloses a suction catheter which substantially eliminates this damage by preventing the invagination of the mucosa into the end or side holes of the catheter while permitting efficient suctioning thereof. As disclosed in the Sackner patent, this improved suction catheter provides an open distal tip and a plurality of apertures extending through the wall of the catheter proximal to the distal tip. A flange extends laterally from the tube adjacent the apertures between the distal opening and the apertures to maintain the apertures spaced from the walls of the body cavity into which the catheter is inserted to prevent occlusion of the apertures upon application of suction.

SUMMARY OF THE INVENTION

Among the several objects of the invention may be noted the provision of a suction catheter which minimizes damage to the mucosa while permitting efficient mucus clearance, and the provision of such a catheter which is characterized by ease of use, simplicity of construction and low cost permitting disposal after a single use.

In general, a suction catheter constructed in accordance with the present invention comprises an elongated tube formed of a flexible material having a lumen running interiorly thereof, the tube having an open distal end for placing the lumen in communication with the interior of a body cavity and a proximal end adapted to place the lumen in communication with a source of pressure lower than that existing at the distal end of the tube. Regulation means are provided for controlling the suction applied at the distal end of the catheter. Plural axially extending flanges are spaced about the distal end of the tube to define alternate raised and depressed surfaces. Apertures in the depressed surfaces between the flanges extend through the wall of the tube into its lumen.

These and other objects and features will be apparent hereinafter.

BRIEF DESCRIPTION OF THE DRAWINGS

Corresponding reference characters indicate corresponding parts throughout the several views of the drawing.

DESCRIPTION OF THE PREFERRED EMBODIMENT

Figure 1:
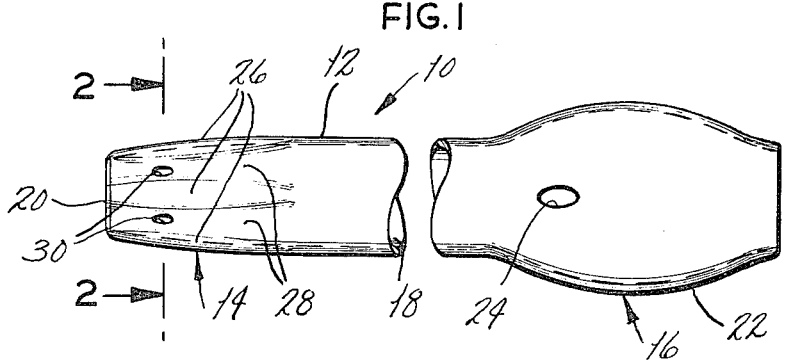
FIG. 1 is an elevational view of a first embodiment of a suction catheter of this invention.
Figure 2:
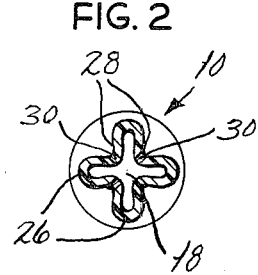
FIG. 2 is a sectional view taken along line 2—2 of FIG. 1.

Referring now to the drawing, and particularly to FIGS. 1 and 2, a suction catheter constructed in accordance with the present invention is indicated generally at 10. The catheter 10 is comprised of an elongated tube 12 having a distal end 14 and a proximal end 16 with a lumen 18 running interiorly thereof defining an opening 20 at the distal tip. The tube 12 may be made of any nontoxic material, preferably a relatively flexible plastic material such as natural or synthetic rubber, polyvinyl chloride, polyethylene, nylon, or the like. The preferable material for ease of manufacture and low cost is polyvinyl chloride.

Any conventional means may be provided at the proximal end 16 of the catheter for connection to a source of pressure lower than that existing at its distal tip opening 20, usually a negative pressure of approximately 40 to 200 mm.Hg. In the embodiment of FIG. 1, an integral bubble connector 22 is illustrated at the proximal end for connection of the catheter 10 to a source of negative pressure (not shown). An eye 24 or any other well-known vacuum regulating means is provided at the proximal end of the catheter so that the user may make and break the negative pressure applied at the distal end of the catheter in a well-known manner. For example, see U.S. Pat. Nos. 3,375,828 and 3,610,242.

The distal end of the catheter is provided with plural axially extending flanges 26 defining alternate raised and depressed surfaces equally spaced around the periphery of the distal end. Flanges 26 extend laterally from the surface of the tube in a radial direction. The depressed areas or valleys 28 between adjacent flanges 26 each have at least one aperture 30 extending through the wall of the tube into its lumen. As illustrated, all surfaces of the distal end of the catheter are smoothly rounded to reduce insertion trauma.

The catheter 10 may be extruded from a thermoplastic material and thereafter heated and postformed in a suitable die to provide the alternate flanges 26 and valleys 28, while the apertures 30 may be punched or drilled after the postforming operation. In the embodiment illustrated in FIGS. 1 and 2, it will be noted that the distal tip is pinched inwardly to form the valleys 28 so that the distal tip tapers slightly inwardly and the flanges 26 and valleys 28 do not exceed the normal outside diameter of the tube 12; that is, the outer diameter of the main tube portion 12 between the ends 14 and 16. This construction provides a suction catheter which does not have an enlargement at the distal tip and facilitates insertion into small body cavities.

The total cross-sectional area of all of the apertures 30 is sufficient to permit only a nominal vacuum to be applied at opening 20 upon application of suction, as will be set forth more fully hereinafter.

Figure 3:
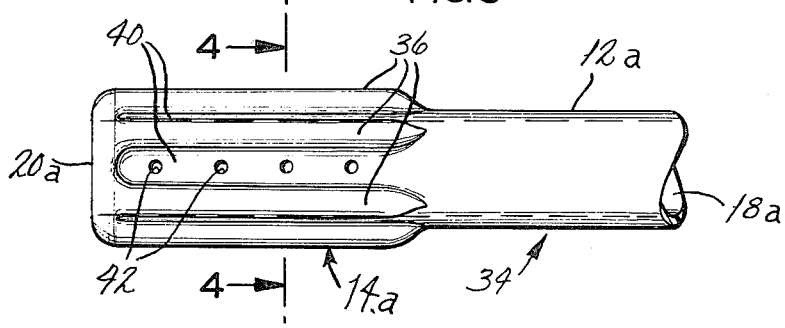
FIG. 3 is a fragmentary elevational view of a second embodiment of the present suction catheter.
Figure 4:
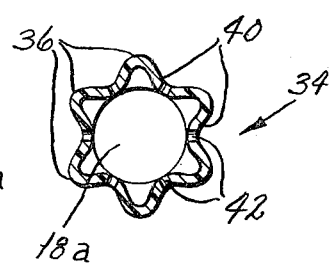
FIG. 4 is a sectional view taken along line 4—4 of FIG. 3.

A suction catheter 34 is illustrated in FIGS. 3 and 4 which is similar to that described in connection with the embodiment of FIGS. 1 and 2 with the exception that the distal end 14a has axially extending lateral flanges 36 which protrude radially above the normal outside diameter of the tube 12a. As shown in FIG. 4, six flanges 36 are equally spaced around the periphery of the distal end of the catheter 34 such that six depressed surfaces or valleys 40 are formed intermediate the flanges along the normal outside diameter of the tube 12a. As illustrated, apertures 42 extend into the lumen 18a through the wall of the tube in the valleys 40. The distal end 14a of this catheter may also be formed in a secondary manufacturing operation by postforming the end of the catheter in a suitable die to form the flanges 36. Again, the total area of the apertures should be sufficient to permit only a nominal vacuum at the opening 20a at the distal tip of the catheter when in use.

Figure 5:
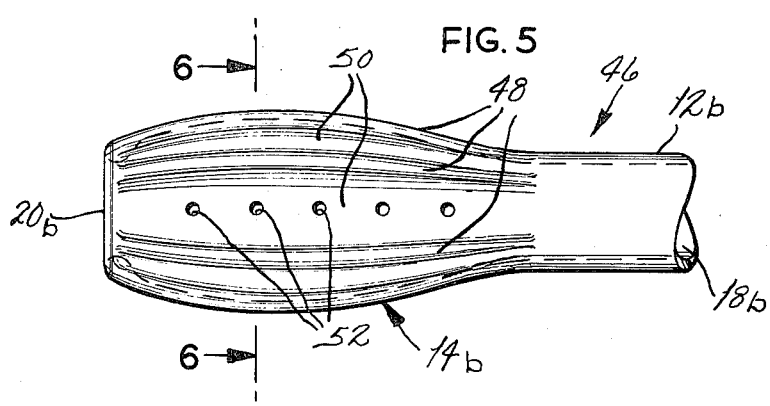
FIG. 5 is a fragmentary elevational view of a third embodiment of the present suction catheter.
Figure 6:
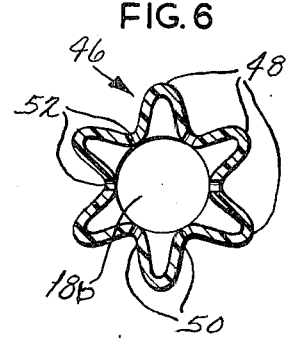
FIG. 6 is a sectional view taken along line 6—6 of FIG. 5.

A suction catheter 46 is shown in FIGS. 5 and 6 which is similar to that illustrated in FIGS. 3 and 4 with the exception that a bubble or enlarged section is formed in the tube during the extrusion process prior to the postforming operation. This bubble may be formed in a conventional manner during the extrusion process, for example, in accordance with the teachings of U.S. Pat. No. 3,674,404. As will be noted, when the tube is extruded with the enlarged bubble portion, the wall thickness at the bubble may be increased. Thereafter, for the postforming operation wherein spaced flanges 48 are formed, additional plastic material is provided to reduce thinning of the walls in the flange 48 and valleys 50. In this construction, the valleys 50, or bottom surfaces of the valleys, as well as the flanges 48, balloon outwardly from the normal outer surface of the main portion of the tube 12b at its distal end 14b. Apertures 52 extend through the wall of the tube 12b in the valleys 50 to communicate with the lumen 18b near distal tip opening 20b.

Figure 7:
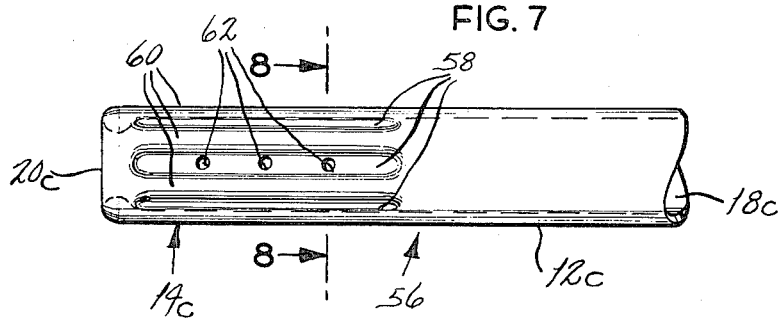
FIG. 7 is a fragmentary elevational view of a fourth embodiment of the present suction catheter.
Figure 8:
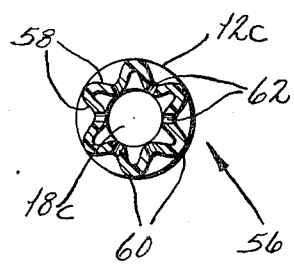
FIG. 8 is a sectional view taken along line 8—8 of FIG. 7.

In the embodiment of the suction catheter 56 illustrated in FIGS. 7 and 8, the valleys 58 are depressed from the normal outside diameter of the tube 12c while the flanges 60 are coextensive with its normal outside diameter to provide a constant outside diameter throughout the length of the distal end and main portions of the tube. Apertures 62 extend through the wall of tube 12c in the valleys 58 to communicate with the lumen 18c and opening 20c. In this embodiment, unlike FIGS. 1 and 2, the distal end 14c of the tube does not taper inwardly.

As will be noted in each of the above embodiments of the present suction catheter, the distal end of the catheter is provided with plural axially extending laterally projecting flanges equally spaced about the circumference of the tube by depressed portions or valleys. Plural apertures extend through the wall of the tube in fluid communication with the lumen between the flanges in the valleys. The catheter has an open distal tip communicating with the tube lumen and vacuum regulating means at its proximal end. In the embodiments of FIGS. 1 and 5, the distal ends of valleys 28 and 50 open into the distal tip of the catheter, while in the FIGS. 3 and 7 embodiments, valleys 46 and 58 terminate short of distal tip 20.

As set forth above, the suction catheters of this invention minimize mucosa damage caused by invagination of the mucosa into the lumen of the catheter upon application of suction. That is, the raised flanges provide a physical barrier preventing the mucosa from being drawn into the side apertures in the depressed valleys and occluding same. Also, total occlusion is prevented by the spacing of the apertures around the entire periphery of the tube. In addition, since the total cross-sectional area of all of the side apertures is sufficient to permit application of only a nominal vacuum at the distal end opening, this opening is prevented from being drawn against a surface of the body cavity during suctioning, such as the tracheobronchial bifurcation. Thus, since the side apertures are prevented from being occluded by the mucosa due to the raised flanges, application of full vacuum at the open distal tip cannot occur as with conventional catheters. For example, for a 14 Fr. suction catheter, the total cross-sectional area of all of the side apertures should be sufficient, as compared to the cross-sectional area of the distal end opening, to produce a negative pressure of only approximately 25 mm.Hg., or less, upon application of approximately 150 mm.Hg. to the catheter. In addition, since the distal end surfaces are smoothly rounded, the catheter cannot cause abrasions as it is inserted and withdrawn along the walls of the body cavity. As shown in the illustrated embodiments, the axial length of the flanges and valleys are of substantial length to insure fluid communication under various operating conditions. While the size of the catheter may vary in accordance with its application, the lengths of the flanges and valleys in the illustrated embodiments are greater than the arcuate distance between the radially outermost points of adjacent flanges, as well as the outer diameter of the main portion of the tube.

If desired, the distal end portion of the tube may be formed such that the bottom surfaces of the valleys are below or radially inwardly of the outer surface of the main tube portion while the radially outermost surfaces of the flanges are above or radially outwardly of the outer surface of the main tube portion.

In view of the above, it will be seen that the several objects and advantages of the invention are achieved and other advantageous results obtained. As various changes could be made in the above constructions without departing from the scope of the invention, it is intended that all matter contained in the above description and shown in the accompanying drawing shall be interpreted as illustrative and not in a limiting sense.

What is claimed is:

1. A suction catheter of a size suitable for insertion into a body cavity containing a gas such as the nose, mouth or larynxgotracheobronchial tree comprising an elongated tube formed of a flexible material having a lumen running interiorly thereof, said tube having an distal end with an opening for placing said lumen in communication with the interior of the body cavity and a proximal end adapted to place said lumen in communication with a source of pressure lower than that existing at the distal end of said tube, regulation means for controlling, from said proximal end, the suction applied at said distal end, said tube being defined by wall portions forming a main body portion and an integral distal end portion of limited length relative to said main body portion, said main body portion being of generally circular cross-section and said lumen being of constant diameter throughout said main body portion, said wall portions forming plural axially extending flanges spaced circumferentially about said distal end portion of said tube and defining alternate raised and depressed surface portions, said wall portions throughout said raised and depressed surface portions being of substantially constant thickness, and apertures in said depressed surface portions between said flanges extending through said wall portions of said tube into said lumen, the total cross-sectional area of all of said apertures being sufficient to permit only a nominal vacuum to be applied at said distal end opening upon application of suction to said catheter.

2. The suction catheter of claim 1 wherein said flanges are equally spaced about said distal end portion of said tube.

3. The suction catheter of claim 2 wherein said apertures extend through said wall portion of said tube at the radially lowest point of said depressed surface portions.

4. The suction catheter of claim 3 wherein a plurality of apertures extend through said wall portion of said tube in each depressed surface portion.

5. The suction catheter of claim 3 wherein said distal end portion of said tube tapers radially inwardly such that said raised and depressed surface portions are radially below the normal outside diameter of said main body portion of said tube.

6. The suction catheter of claim 3 wherein said distal end portion of said tube is enlarged such that said flanges extend radially above the normal outside diameter of said main body portion of said tube.

7. The suction catheter of claim 6 wherein the lowermost portion of said depressed surfaces are coextensive with the normal outside diameter of said main body portion of said tube.

8. The suction catheter of claim 3 wherein said distal end portions of said catheter are coextensive with the normal outside diameter of said tube and said depressed surface portions extend radially below the normal diameter of said main body portion of said tube.

9. The suction catheter of claim 1 wherein said flanges extend axially of said tube a distance greater than the distance between the radially outermost points on adjacent flanges.

10. The suction catheter of claim 1 wherein the lengths of said flanges are greater than said diameter of said main body portion of the tube.

* * * * *